United States Patent
Falkenberg

(10) Patent No.: US 11,433,204 B2
(45) Date of Patent: Sep. 6, 2022

(54) TRACHEOSTOMA DEVICE HOLDER

(71) Applicant: Atos Medical AB, Horby (SE)

(72) Inventor: Richard Falkenberg, Horby (SE)

(73) Assignee: Atos Medical AB

( * ) Notice: Subject to any disclaimer, the term of this patent is extended or adjusted under 35 U.S.C. 154(b) by 469 days.

(21) Appl. No.: 16/075,649

(22) PCT Filed: Oct. 27, 2016

(86) PCT No.: PCT/SE2016/051044
§ 371 (c)(1),
(2) Date: Aug. 4, 2018

(87) PCT Pub. No.: WO2017/135861
PCT Pub. Date: Aug. 10, 2017

(65) Prior Publication Data
US 2019/0046750 A1    Feb. 14, 2019

(30) Foreign Application Priority Data

Feb. 4, 2016    (SE) .................................. 1650137-1

(51) Int. Cl.
*A61M 16/04* (2006.01)
*A61M 16/06* (2006.01)

(52) U.S. Cl.
CPC ....... *A61M 16/047* (2013.01); *A61M 16/0688* (2014.02)

(58) Field of Classification Search
CPC . A61M 16/0465–0472; A61M 16/0683–0688; A61M 2025/0266; A61F 2/02; A61F 2/20; A61F 2/203; A61F 2002/046; A61F 2013/00978; A61F 5/44;
(Continued)

(56) References Cited

U.S. PATENT DOCUMENTS

| 4,419,100 A * | 12/1983 | Alexander | ............. A61F 5/448 604/339 |
| 4,846,820 A * | 7/1989 | Jensen | .................... A61F 5/445 604/339 |

(Continued)

FOREIGN PATENT DOCUMENTS

| JP | 2015-536220 A | 12/2015 |
| WO | WO-99/29268 A1 | 6/1999 |
| WO | 2014090549 A1 | 6/2014 |

OTHER PUBLICATIONS

Japanese Office Action related to corresponding Japanese Patent Application No. 2018-536290.

*Primary Examiner* — Elliot S Ruddie
(74) *Attorney, Agent, or Firm* — Fishman Stewart PLLC

(57) ABSTRACT

A tracheostoma device holder for holding a tracheostoma aid device superimposed on a tracheostoma of a person is provided. The tracheostoma device holder may comprise a skirt for attachment over a tracheostoma via a skin adhesive proximal side thereof, wherein the skirt is provided with a through hole. The tracheostoma device holder may comprise a tubular tracheostoma device fitting arranged circumferentially of the through hole. The tubular tracheostoma device fitting may comprise a sleeve extending distally from a distal side of the skirt, and an annular lip. The lip may extend proximally and centrally from the sleeve.

20 Claims, 3 Drawing Sheets

(58) Field of Classification Search
CPC ..... A61F 5/4401–448; A61F 2005/4415–4486
USPC ................. 128/207.14–207.17; 604/332–344
See application file for complete search history.

(56) References Cited

U.S. PATENT DOCUMENTS

| | | | | |
|---|---|---|---|---|
| 5,195,996 | A * | 3/1993 | Edwards | A61F 5/448 |
| | | | | 604/332 |
| 5,718,696 | A * | 2/1998 | Kollerup | A61F 5/443 |
| | | | | 604/339 |
| 5,738,095 | A * | 4/1998 | Persson | A61F 2/20 |
| | | | | 128/201.13 |
| 7,025,784 | B1 * | 4/2006 | Blom | A61F 2/20 |
| | | | | 623/14.11 |
| 9,943,436 | B2 * | 4/2018 | Nguyen-Demary | A61F 5/448 |
| 10,456,289 | B2 * | 10/2019 | Alden | A61F 5/4405 |
| 2003/0204174 | A1 * | 10/2003 | Cisko, Jr. | A61F 5/445 |
| | | | | 604/338 |
| 2005/0277901 | A1 | 12/2005 | Gijsbert Van Der Leden | |
| 2007/0283962 | A1 | 12/2007 | Doshi et al. | |
| 2013/0192604 | A1 * | 8/2013 | Persson | A61M 16/047 |
| | | | | 128/207.16 |
| 2015/0306327 | A1 * | 10/2015 | Persson | A61M 16/047 |
| | | | | 128/200.26 |
| 2015/0359658 | A1 * | 12/2015 | Leise, Jr. | A61F 5/448 |
| | | | | 604/342 |

* cited by examiner

TRACHEOSTOMA DEVICE HOLDER

CROSS REFERENCE TO RELATED APPLICATIONS

This application claims priority to International Application PCT/SE2016/051044 filed on Oct. 27, 2016 and Swedish Application SE 1650137-1 filed on Feb. 4, 2016, the contents of each of which are hereby incorporated by reference in their entirety.

FIELD OF THE INVENTION

This invention pertains in general to a tracheostoma aid device holder. More particularly, the present invention pertains to a tracheostoma aid device holder, comprising a skirt for attachment over a tracheostoma via the proximal side of the skirt, said skirt being provided with a through hole having a tubular tracheostoma device fitting extending distally from the skirt circumferentially of said through hole.

BACKGROUND OF THE INVENTION

A tracheostomy is a surgical procedure in which an opening is formed through the anterior surface of the neck into the trachea. The opening is referred to as a tracheostoma. A tracheostomy tube can be provided to extend between the tracheostoma and the trachea. A tracheostomy is performed for example when there is a malfunction, such as a result from injury or disorder, in respect of the nervous system or the respiratory passages, which malfunction results in an incapacity to obtain enough air. An inferior lung capacity or need of respiratory treatment may also result in a tracheostomy.

A laryngectomy is a surgical procedure, used for example to treat a carcinoma, which involves removal of the larynx or voice box and the creation of a tracheostoma. A consequence of the procedure is that the trachea is no longer connected to the pharynx but is diverted to the tracheostoma. After this procedure, normal nasal function is not possible. In a subject whose breathing functions normally, the nose and the mucous membrane lining of the nasal cavity perform important functions in conditioning inhaled air. The convoluted passages and rich blood supply serve to increase both the temperature and humidity of the inhaled air to minimise the differential in these parameters with those of the surface of the lungs. Normally some heat and moisture is also captured from exhaled air prior to its release to the atmosphere. The mucous lining of the nasal passages also serves to remove particulate matter, such as fine dust particles, pollutants and microorganisms, from the inhaled air, and the action of cilia transports mucous and any particles away from the lungs.

When a person has received a laryngectomy, in effect all inhaled air enters the lungs via the tracheostoma, and the nose is effectively not involved in the inhalation process. Exhaled air may pass through the tracheostoma or, if a voice prosthesis has been fitted, the stoma can be occluded so that the exhaled air is diverted through the voice prosthesis into the pharynx and the mouth, enabling the person to speak. It is desirable that the flow of the exhaled air be controlled by means of a tracheostoma valve. In these situations, the valve can be arranged to remain open during breathing but can be closed to divert the airflow, through a small additional increase in exhaled air flow.

In this respect tracheostoma aid devices, such as filter devices, HME, breathing protectors, and speech valves, have been developed to enable moisturizing of inhaled air, removal of small particles and bacteriological substances in said inhaled air, and providing the person with the ability to speech by closing the air passage through the tracheostoma by manual operation.

These tracheostoma aid devices are held in place by a tracheostoma device holder, arranged above the tracheostoma of the person. The tracheostoma device holder is normally attached to the skin of the person by a plaster, having an adhesive surface on the side of the plaster intended to be directed towards the person in use. Either, the tracheostoma device holder is welded to the plaster, or the tracheostoma device holder is arranged on an adhesive surface on the side of the plaster intended to be directed outwards from the person in use. On the skin adhesive surface a covering sheet/foil may be applied, which is removed just before application of the tracheostoma device holder. The covering sheet facilitates transportation, and maintains skin adhesive ability of the skin adhesive surface.

A tracheostoma device holder of this kind is disclosed in U.S. Pat. No. 7,025,784, wherein the device comprises a cylindrical sleeve, an annular flexible and resilient skirt projecting outward from an outside wall of the sleeve, said skirt being configured for attachment to the skin of a wearer around the tracheostoma. The device holder may hold a tracheostoma aid device, wherein either the tracheostoma device holder or the tracheostoma aid device includes an annular recess on the side wall thereof and the other of the two comprises an annular rib, wherein the recess and the rib ensures engagement between the two. A disadvantage with this device holder is that the tracheostoma aid device will be released once a retaining force threshold is overcome by exhaled air pressure. Also, the sealing effect between the tracheostoma device holder and the tracheostoma aid device will also be affected by the retaining force threshold, such that the risk of unwanted air leakage between the tracheostoma device holder and the tracheostoma aid device is increased, which will negatively affect the possibility to control for example air flow through a voice prosthesis in the oesophageal/tracheal wall.

Hence, an improved tracheostoma device holder would be advantageous, and in particular a tracheostoma device holder allowing for convenient application of the tracheostoma device holder with improved retaining and sealing effect between the tracheostoma device holder and the tracheostoma aid device.

SUMMARY OF THE INVENTION

Accordingly, the present invention preferably seeks to mitigate, alleviate or eliminate one or more of the above-identified deficiencies in the art and disadvantages singly or in any combination and solves at least the above mentioned problems by providing a tracheostoma device holder for holding a tracheostoma aid device superimposed of a tracheostoma of a person, said tracheostoma device holder comprising a skirt for attachment over a tracheostoma via a proximal side of the skirt, said skirt being provided with a through hole having a tubular tracheostoma device fitting, said tubular tracheostoma device fitting comprising a sleeve extending distally from the skirt circumferentially of said through hole, said tubular tracheostoma device fitting comprising an annular lip extending proximally and centrally from the sleeve.

A tracheostoma aid device for placement in such a tracheostoma device holder is also provided.

Advantageous features of the invention are defined in the dependent claims.

BRIEF DESCRIPTION OF THE DRAWINGS

These and other aspects, features and advantages of which the invention is capable of will be apparent and elucidated from the following description of embodiments of the present invention, reference being made to the accompanying drawings, in which

FIG. 3a is a cross-sectional view of a tracheostoma device holder and tracheostoma aid device taken though the section A-A in FIG. 2.

FIG. 3b is a cross-sectional view of a tracheostoma device holder and tracheostoma aid device showing a detailed view of the region B in FIG. 3a.

DESCRIPTION OF EMBODIMENTS

The following description focuses on an embodiment of the present invention applicable to a tracheostoma device holder 100, for holding a tracheostoma aid device 200 over the stoma of a person. A tracheostoma aid device 200 may in this context be a tracheostoma valve, HME, speech valve, etc., or combinations thereof.

Figure 1:
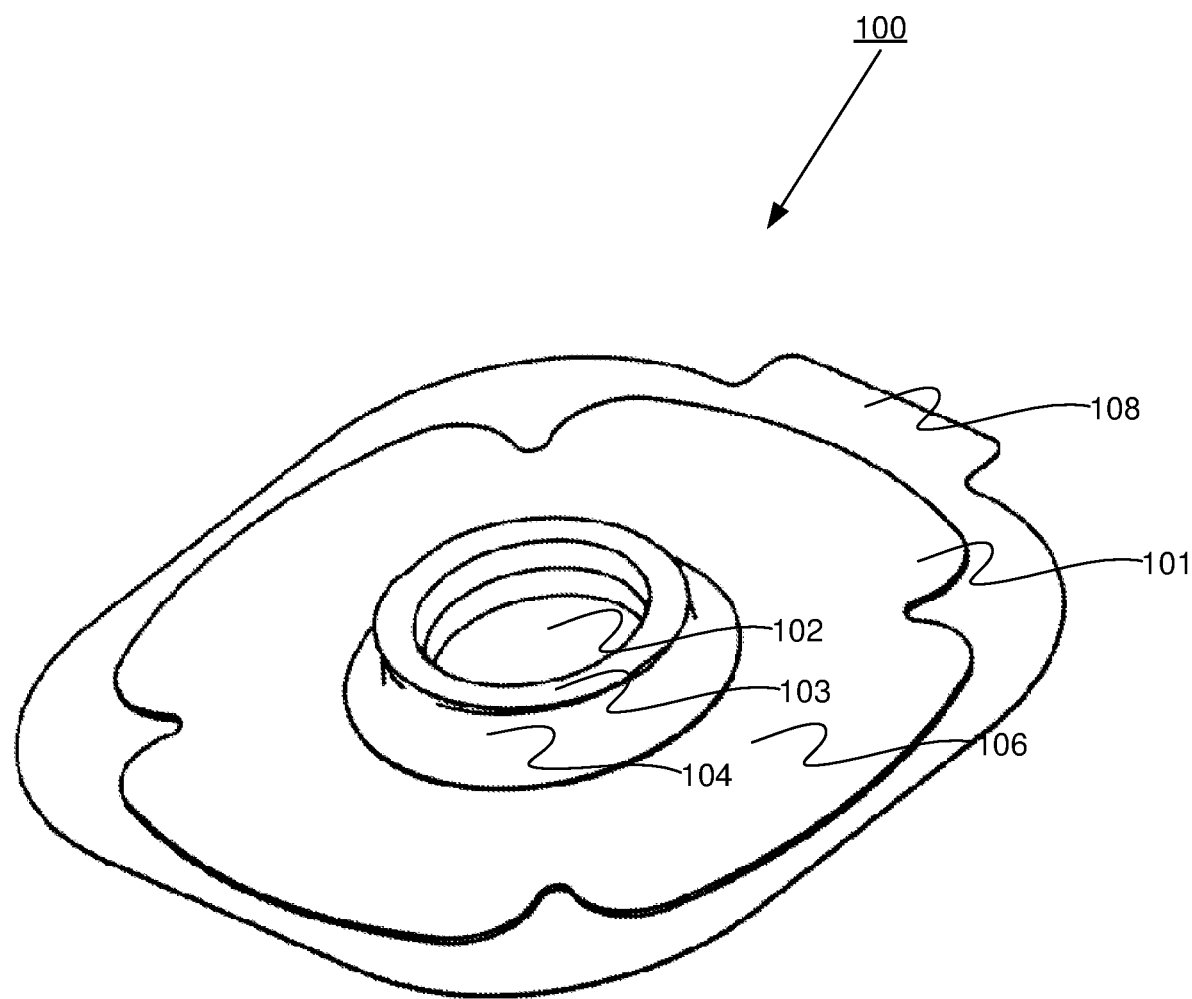
FIG. 1 is an isometric view of the tracheostoma device holder according to an embodiment of the invention.
Figure 2:
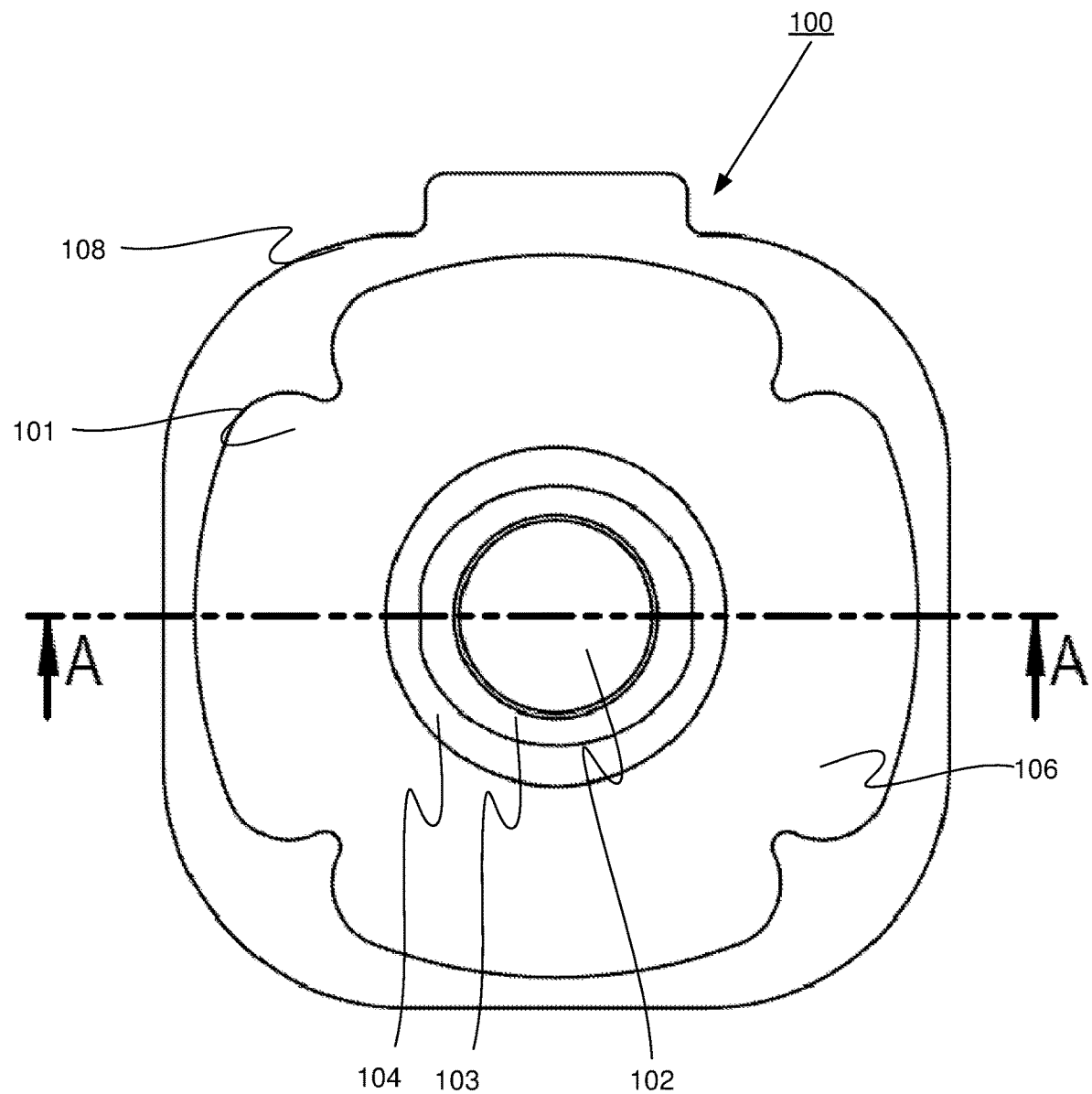
FIG. 2 is a perspective front-view of a tracheostoma device holder according to an embodiment of the invention.
Figure 3:
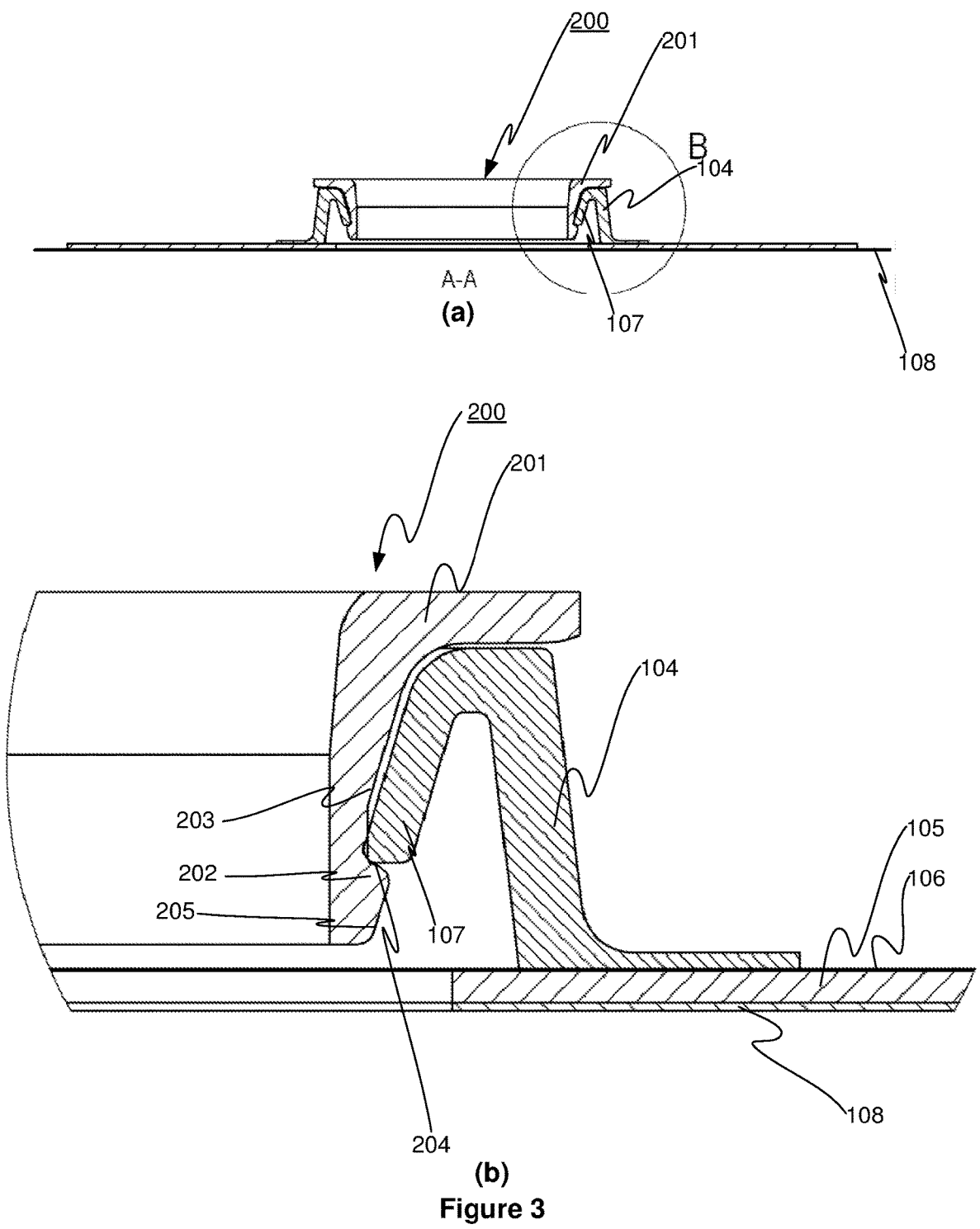

In FIGS. 1 to 3 a tracheostoma device holder 100 for holding a tracheostoma device superimposed of a tracheostoma of a person is disclosed. The tracheostoma device holder 100 comprises a skirt 101 for attachment over a tracheostoma via a skin adhesive proximal side thereof. The skirt 101 is preferably flexible. The skirt 101 is provided with a through hole 102. The tracheostoma device holder 100 also comprises a tubular tracheostoma device fitting 103. The tubular tracheostoma device fitting 103 is arranged circumferentially of the through hole 102. The tubular tracheostoma device fitting 103 extends distally from the distal side of the skirt 101. To this end, the tubular tracheostoma device fitting 103 comprises a sleeve 104, extending distally from the distal side of the skirt 101. The skirt 101 may comprise a proximal end sheet 105. The proximal end sheet 105 may comprise, such as for example consisting of, a skin adhesive hydrogel or hydrocolloid. When the proximal end sheet 105 comprises a skin adhesive hydrogel or hydrocolloid the skin underneath the skirt may be allowed to exude sweat without significant loss of skin adherence between skin and tracheostoma device holder 100. Hydrogels contain a large quantity of water already, which allows them to tolerate the additional water from sweat. Also, the compressibility, flexibility and formability allows for the proximal end sheet 105 to take up discrepancies in skin structure and allow for easy stoma access.

Distally of—such as adjacent and attached to—the proximal end sheet 105 a distal support sheet 106 is provided. The distal support sheet 106 is preferably of a material allowing for the skin underneath the tracheostoma device holder 100 to continue breathing, not only through the proximal end sheet 105 but also through the distal support sheet 106. Additionally, it should be compatible with the proximal end sheet 105 comprising hydrogel or hydrocolloid as well as maintaining the compressibility, flexibility and formability of the proximal end sheet 105. For these purposes it has been found that the distal support sheet 105 preferably comprises, such as consists of, polyurethane.

The tracheostoma device fitting 103 is made of a flexible and resilient material, such as rubber or silicone. In such configuration, the skirt 101 will extend laterally as a flange from the tubular tracheostoma device fitting 103, in relation to a central axis of the through hole 102. Similarly, the tubular tracheostoma device fitting 103 extends axially and distally from the skirt 101, in accordance with above.

The tracheostoma device fitting 103 also comprises a lip 107. The lip 107 is annular. The lip 107 extends proximally and centrally from the sleeve 104. The lip may extend from the distal end zone of the sleeve 104, such as from the distal end of the sleeve 104. When the lip extends from the distal end of the sleeve 104, the manufacturing of the tracheostoma device holder 100 is facilitated and also the flexibility and length of the lip 107 may be adapted more freely to the relevant circumstances, i.e. the resistance force when placing the tracheostoma aid device 200 in the tracheostoma device fitting 103, the sealing force as a result of pressure difference between trachea and surroundings, and sealing force between the lip 107 and the tubular body 201 may be adapted after needs. To this end, the lip 107 extends proximally and centrally from the inner/central side wall of the sleeve 104. This inner/central side wall of the sleeve extends axially with the trough hole 102, defining the lumen of the tracheostoma device fitting 103. The proximally and centrally extending lip 107 will form a cavity laterally of the lip 107, i.e. in between the lip 107 and the sleeve 104. Because of this, the lip 107 will be able to flex outwardly/laterally upon pushing a tracheostoma aid device 200 into the tracheostoma device fitting 103.

The tracheostoma aid device 200 is provided with a tubular body 201 and a heel 202 at its proximal end zone, such as at the proximal end of the tracheostoma aid device 200. The heel 202 is continuously or discontinuously annular at the outer/lateral wall 203 of the tracheostoma aid device 200. The heel 202 is preferably provided with a distal ledge 204, extending perpendicularly to the central axis of the tracheostoma aid device 200 and/or the outer/lateral wall 203 of the tracheostoma device 200. The proximal end surface 205 of the heel 202 is preferably slanting inwardly/centrally. In this way, the proximal end surface 205 of the heel 202 may continuously push the lip 107 laterally/outwardly upon insertion of the tracheostoma aid device 200 into the tracheostoma device fitting 103, where after the lip will snap centrally/inwardly distally of the ledge 204 of the heel 202. In this position, the lip 107 may seal against the outer/lateral wall 203 of the tracheostoma aid device 200—especially upon high pressure differences between the surroundings and the trachea. Due to this configuration, the retaining force and sealing effect will increase as the pressure difference between the surroundings and the trachea increases, since the distally directed force will push the lip 107 centrally/inwardly.

When removing/releasing the tracheostoma aid device 200 from the tracheostoma device holder 100, the tracheostoma aid device 200 is first displaced laterally in relation to the tracheostoma device holder 100, until the heel 202 passes the lip 107 on one side of the arrangement of cooperation between the tracheostoma aid device 200 and the tracheostoma device holder 100. In this position, the heel 202 on the other side of the arrangement is in closer cooperation. Once the heel 202 passes the lip 107 the tracheostoma aid device 200 may be rotated upwards to be released from its cooperation with the tracheostoma device holder 100.

Proximally of the proximal end sheet 106 a protective lining 108 may be applied, which is removed before use, i.e. attachment over the stoma and to the skin surrounding the stoma of the patient.

Although the present invention has been described above with reference to specific embodiments, it is not intended to be limited to the specific form set forth herein. Rather, the invention is limited only by the accompanying claims and, other embodiments than the specific above are equally possible within the scope of these appended claims.

In the claims, the term "comprises/comprising" does not exclude the presence of other elements or steps. Furthermore, although individually listed, a plurality of means, elements or method steps may be implemented by e.g. a single unit or processor. Additionally, although individual features may be included in different claims, these may possibly advantageously be combined, and the inclusion in different claims does not imply that a combination of features is not feasible and/or advantageous. In addition, singular references do not exclude a plurality. The terms "a", "an", "first", "second" etc do not preclude a plurality. Reference signs in the claims are provided merely as a clarifying example and shall not be construed as limiting the scope of the claims in any way.

The invention claimed is:

1. A tracheostoma coupling system, comprising:
   a tracheostoma aid device;
   a tracheostoma device holder for holding the tracheostoma aid device superimposed on a tracheostoma of a person, wherein the tracheostoma device holder comprises:
   a skirt for attachment over the tracheostoma via a skin adhesive proximal side of the skirt, wherein the skirt is provided with a through hole;
   a tubular tracheostoma device fitting arranged circumferentially around the through hole, wherein the tubular tracheostoma device fitting comprises a sleeve extending distally from a distal side of the skirt, and an annular lip, the annular lip extending proximally and centrally from the sleeve;
   wherein the annular lip engages against an outer lateral wall of the tracheostoma aid device to facilitate sealing and retaining of the tracheostoma aid device; and
   wherein the annular lip extends proximally and centrally from an inner central side wall of the sleeve to form a cavity laterally of the annular lip and between the annular lip and the inner central side wall of the sleeve, such that the outer lateral wall of the tracheostoma aid device is displaced laterally in relation to the tracheostoma device holder during removal of the tracheostoma aid device from the tracheostoma device holder.

2. The tracheostoma coupling system according to claim 1, wherein the annular lip ends distally of the distal side of the skirt.

3. The tracheostoma coupling system according to claim 1, wherein the annular lip extends from a distal end zone of the sleeve that includes a distal end of the sleeve.

4. The tracheostoma coupling system according to claim 1, wherein the skirt comprises a proximal end sheet.

5. The tracheostoma coupling system according to claim 4, wherein the proximal end sheet comprises a skin adhesive hydrogel or hydrocolloid.

6. The tracheostoma coupling system according to claim 4, wherein a distal support sheet is provided distally of the proximal end sheet.

7. The tracheostoma coupling system according to claim 6, wherein the distal support sheet comprises polyurethane.

8. The tracheostoma coupling system according to claim 6, wherein the annular lip extends from a distal end zone of the sleeve to a free end that ends distally of the distal support sheet.

9. The tracheostoma coupling system according to claim 1, wherein the tracheostoma device fitting is made of a flexible and resilient material that includes rubber or silicone.

10. The tracheostoma coupling system according to claim 1, wherein the skirt extends laterally as a flange from the tubular tracheostoma device fitting, in relation to a central axis of the through hole, and the tubular tracheostoma device fitting extends axially and distally from the skirt.

11. The tracheostoma coupling system according to claim 1, wherein the tracheostoma aid device comprising a tubular body with a central axis, the outer lateral wall, and a heel at a proximal end zone of the tubular body.

12. The tracheostoma coupling system according to claim 11, wherein the heel is continuously annular at the outer lateral wall.

13. The tracheostoma coupling system according to claim 11, wherein the heel is provided with a distal ledge, extending perpendicularly to the central axis, and wherein a free end of the annular lip is configured to engage against the outer lateral wall distally of the distal ledge of the heel once the heel passes the lip upon insertion of the tracheostoma aid device into the tracheostoma device fitting.

14. The tracheostoma coupling system according to claim 11, wherein a proximal end surface of the heel is slanted inwardly relative to the central axis towards the through hole.

15. The tracheostoma coupling system according to claim 1, wherein the outer lateral wall of the tracheostoma aid device has an outer surface that is slanted outwardly relative to the central axis in a distal direction.

16. A tracheostoma coupling system, comprising:
   a tracheostoma aid device including a heel at a proximal end of the tracheostoma aid device;
   a tracheostoma device holder for holding the tracheostoma aid device superimposed on a tracheostoma of a person, wherein the tracheostoma device holder comprises:
   a skirt for attachment over the tracheostoma via a skin adhesive proximal side of the skirt, wherein the skirt is provided with a through hole;
   a tubular tracheostoma device fitting arranged circumferentially around the through hole, wherein the tubular tracheostoma device fitting comprises a sleeve and an annular lip; and
   wherein the sleeve extends distally from a distal side of the skirt, and the annular lip extends proximally and centrally from an inner central side wall of the sleeve and ends distally of the distal side of the skirt and engages against an outer lateral wall of the tracheostoma aid device to facilitate sealing and retaining of the tracheostoma aid device, and wherein the proximally and centrally extending annular lip forms a cavity laterally of the annular lip and between the annular lip and the inner central side wall of the sleeve, such that the outer lateral wall of the tracheostoma aid device is configured to be displaced laterally in relation to the tracheostoma device holder while the heel interacts with the annular lip during removal of the tracheostoma aid device from the tracheostoma device holder.

17. The tracheostoma coupling system according to claim 16, wherein the annular lip extends from a distal end zone of the sleeve that includes a distal end of the sleeve.

18. The tracheostoma coupling system according to claim 16, wherein the skirt comprises a proximal end sheet, and a distal support sheet is provided distally of the proximal end sheet; and
  wherein the annular lip has a free end that ends distally of the distal support sheet.

19. The tracheostoma coupling system according to claim 16, wherein the heel is provided with a distal ledge, extending transversely to a central axis of the tracheostoma aid device, and wherein a free end of the annular lip is configured to engage against the outer lateral wall distally of the distal ledge of the heel once the heel passes the lip upon insertion of the tracheostoma aid device into the tracheostoma device fitting.

20. The tracheostoma coupling system according to claim 19, wherein a proximal end surface of the heel is slanted inwardly relative to the central axis towards the through hole.

* * * * *